United States Patent [19]

Kar

[11] Patent Number: 4,610,797

[45] Date of Patent: Sep. 9, 1986

[54] METALLO-ORGANO ALUMINATES AS LUBRICANT ADDITIVES

[75] Inventor: Kishore K. Kar, Midland, Mich.

[73] Assignee: The Dow Chemical Company, Midland, Mich.

[21] Appl. No.: 737,314

[22] Filed: May 24, 1985

Related U.S. Application Data

[63] Continuation-in-part of Ser. No. 619,442, Jun. 11, 1984, Pat. No. 4,519,924.

[51] Int. Cl.⁴ .......................................... C10M 129/26
[52] U.S. Cl. ........................................ 252/35; 252/36; 252/41; 252/184
[58] Field of Search .............................. 252/35, 36, 41

[56] References Cited

U.S. PATENT DOCUMENTS

| | | | |
|---|---|---|---|
| 4,280,914 | 7/1981 | Pratt | 252/35 |
| 4,348,295 | 9/1982 | Burba, III | 252/184 |
| 4,348,297 | 9/1982 | Bauman et al. | 252/184 |

Primary Examiner—Jacqueline V. Howard
Attorney, Agent, or Firm—W. J. Lee

[57] ABSTRACT

Crystalline aluminates conforming substantially to the general formula $LiR.2Al(OH)_3$, $CaR(A).2Al(OH)_3$, or $ZnR(A).2Al(OH)_3$, where R is an organic acid of $C_6$–$C_{22}$ and A, when present, is an inorganic anion, are found to improve the coefficient of friction and antiwear properties of lubication fluids subjected to shearing, rubbing, or grinding forces at elevated pressure.

17 Claims, 3 Drawing Figures

METALLO-ORGANO ALUMINATES AS LUBRICANT ADDITIVES

CROSS-REFERENCE TO RELATED APPLICATION

This is a continuation-in-part of pending application Ser. No. 619,442, filed June 11, 1984, now U.S. Pat. No. 4,519,924.

BACKGROUND OF THE INVENTION

Crystalline aluminate compositions conforming generally to the empirical formula $Li^+(RCOO^-).2Al(OH)_3.nH_2O$, where $RCOO^-$ represents an organic acid anion, and $nH_2O$ represents any waters of hydration, are disclosed, inter alia, in U.S. Pat. Nos. 4,348,295, 4,348,296, and 4,348,297. These three patents are incorporated herein by reference.

The following patents are believed to be representative of the most relevant art regarding extreme pressure lubricant additives: U.S. Pat. Nos. 2,621,159; 3,001,939; 3,093,584; 3,318,808; 3,565,802; 3,909,426; 3,984,599; 3,997,454; and 4,293,430.

In these relevant arts the principles of the following tests, or variations thereof, are usually followed:

ASTM D-2509 "Standard Method for Measurement of Extreme Pressure Properties of Lubricating Grease (Timken Method)".

ASTM D-2782 "Standard Method for Measurement of Extreme Pressure Properties of Lubricating Fluids (Timken Method)".

ASTM D2783 "Standard Method for Measurement of Extreme Pressure Properties of Lubricating Fluids (Four-Ball Method)".

In this present disclosure the expression "lithium stearate aluminate"(a.k.a. "LSA") is a crystalline compound of the above formula, $Li^+(RCOO^-).2Al(OH)_3.nH_2O$, where $RCOO^-$ is the negative-valent carboxylate radical of stearic acid. It is prepared in accordance with the procedure disclosed in U.S. Pat. No. 4,348,295 or U.S. Pat. No. 4,348,297 whereby crystalline $LiOH.2Al(OH)_3.nH_2O$, material is reacted with stearic acid, thereby replacing the $OH^-$ (attached to the Li) with $RCOO^-$.

Lithium stearate aluminates (LSA) are organic-inorganic (60:40) hybrid crystalline materials conforming substantially to the empirical formula $LiX.2Al(OH)_3.nH_2O$, where X is an anion (stearate) and $nH_2O$ represents water of hydration. These are 2- or 3-layer unit cell structures. The particle size is usually from about 150 Å to about 5000 Å. TGA studies have shown that it decomposes at 300° C. X-ray defraction and SEM analyses have revealed its platelet structure.

Industrial oils and lubricating fluids frequently require friction reducers for energy saving and antiwear/extreme pressure additives to extend their functional range. Tribological research has now been conducted to evaluate the lubrication performance of lithium stearate aluminate as an additive in lubricants. The place of LSA within the lubricant industry is found, e.g., in its application as an extreme pressure (EP), anti-wear and friction-reducing additive.

Extreme pressure (EP) and anti-wear additives are used mainly to improve the performace of lubricants. As a class, such substances produce a physical or chemical effect on the surfaces of the friction pair, thus leading to a reduction in wear rate under conditions of mixed or boundary lubrication and an increase in the seizure load. Such additives are called extreme pressure and antiwear additives.

The principal effect of an EP additive occurs under heavy loads when, in addition to high temperatures, the metallic surface is activated mechanically (tribo-chemical effect). It is known that freshly worn surfaces are a source of electrons which are capable of initiating several reactions which would otherwise not occur. In some cases, the additive or additives present in the lubricant, in contact with the frictional surface at high temperatures, undergo polymerization or reaction with one another leading to the formation of a solid compound on the surface. The polymer layer formed by the insitu polymerization at high temperature, affords protection of the metallic surfaces against corrosion, serving as an antioxidant.

It is well known that some extreme pressure additives such as chlorinated paraffins, sulfo-chlorinated oils, or zinc dithiophosphates react with metallic surfaces during the frictional process. The reaction layer may improve the frictional properties of the metallic surfaces if it is a low shear strength compound or may simply prevent direct contact between the surfaces and the formation of junctions. Reaction between the metallic surface and the additive may also reduce adhesion. At the point of contact between the surfaces where the temperature is high, the additive prevents the formation of an adhesion bridge by reacting with the metallic surface. As asperities are the initial contact points, the process may lead to polishing of the surface (chemical polishing). Some of the EP additives (e.g. Zn-dithiophosphates) also possess antioxidant characteristics having two or more active elements in their molecules.

If the effectiveness of EP and antiwear additives is due to the reaction layer formed on the metallic surfaces in contact, additive reactivity should be controlled, that is, the reaction between the metallic surface and the additive should take place only on the friction surface. Excessive reactivity may cause corrosion while low reactivity may not permit the formation and preservation of a protective layer on the surfaces of the friction pair as the existence of the layer in the contact area is the result of an equilibrium between the formation and wear processes. For this reason, chlorinated paraffin oils have limited use as antiwear-extreme pressure additive. It is reported that the presence of chlorinated-type additives in metal-working fluids often initiate corrosion of the machines over a long period of idleness. Some chlorine and sulfur base additives are reported to irritate skin or produce foul odors.

Long chain lubes such as the esters of fatty acids, aliphatic alcohols, and amines are used as friction reducers and antiwear additives in lubricants. A characteristic or their effectiveness is determined by the stability of the layer on the frictional surface. Usually at relatively low temperatures up to 150° C., the layer is desorbed, losing its effectiveness. The melting points of most of the long chain lubes (metallic soaps) are less than 150° C. For effective lubrication above 150° C., surface films withstanding higher temperatures must be used. Some lamellar solids, such as graphite and molybdenum disulfide, having low intrinsic shear strength because of their layer lattice crystal structure, are used as solid lubricants. The lubrication effectiveness is attributed to the formation of an adhering film rather than a reactive film. Solid lubricants are well known as friction reducers. Crystalline lithium aluminates (stearic anion) decompose at 300° C., whereas MoS2 and graphite melt at 400° C. and 500° C.

The particle size usually affects the lubricating properties of the suspension. Experimental work carried out on a four-ball tester has shown that if colloidal suspensions are used, the optimum mean diameter of the MoS2 particle is around 25,000 Å. A complex interdependence exists between particle size and the antiwear characteristics of the suspension. Under light loads particle size has no effect, while under heavy loads larger grain sizes usually result in increased wear.

It was disclosed in Ser. No. 619,442, filed June 11, 1984, that crystalline lithium stearate aluminate (LSA) significantly improves the friction resistance, the antiwear properties, and the extreme pressure (EP) properties of lubrication fluids that are subjected to shearing, rubbing, or grinding forces at significantly elevated pressures.

SUMMARY OF THE INVENTION

Compounds corresponding essentially to the following described formulae have been found to improve lubrication fluids subjected to shearing, rubbing, or grinding forces at significantly elevated pressures:

$\text{Li}(R)_r^v \cdot 2\text{Al}(OH)_3 \cdot n\text{H}_2\text{O}$,    I.

and

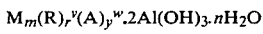
$M_m(R)_r^v(A)_y^w \cdot 2\text{Al}(OH)_3 \cdot n\text{H}_2\text{O}$    II.

where
$n\text{H}_2\text{O}$ represents any waters of hydration that may be present;
R represents a monocarboxylic acid or dicarboxylic acid of $C_6-C_{22}$, including those which are OH-substituted;
r is greater than zero and represents the number of R ions in the molecule;
v is the valence of R, being monovalent or divalent;
M is divalent Zn or Ca cations;
A represents inorganic anions of valence 1–3, represented by w;
y is equal to or greater than zero and represents the number of A anions;
wherein, in formula I, vr represents an amount of R anions to substantially satisfy the valence requirements of Li;
wherein, in formula II, r>y and (vr+wy) represents an amount of combined anions, R and A, to substantially satisfy the valence requirements of M;
with m representing the number of divalent M cations and having a numerical value in the range of about 1 to about 4.

DETAILED DESCRIPTIONS

The lithium stearate aluminate (LSA) conforms substantially to the formula (as in U.S. Pat. Nos. 4,348,295 and 4,348,297) illustrated empirically as

cryst. $\text{LiX} \cdot 2\text{Al}(OH)_3 \cdot n\text{H}_2\text{O}$, where X is the stearic radical and where n may be zero or more for the waters of hydration. The aluminate crystal may be of the two-layer or three-layer variety or may be a mixture of the two varieties. Related compounds, as described in the Summary, in formula I, above may also be employed as a lubricant additive the same way as LSA by using $C_6-C_{22}$ acids other than stearic acid, such as 12-hydroxy stearic acid, adipic acid, behenic acid, and the like.

Compounds of formula II in the summary above are prepared from layered crystalline compounds of the formula $M_m A_y^w \cdot 2\text{Al}(OH)_3$, where M is Ca or Zn, where A represents inorganic anions of valence (w) of 1 to 3, where y represents a quantity of A ions to substantially satisfy the valence requirements of M, and where M represents an amount in the range of 1–4. This is done by mixing it with the desired carboxylic acid in aqueous or alcoholic medium thereby replacing some or all of the inorganic ions with R ions.

The symbol "A" in Formula II represents an inorganic anion of valence 1 to 3 which, when combined with M cations forms a salt, e.g., sulfate, hydroxide, phosphate, hydrogen phosphate, chloride, bromide, carbonate, nitrate, or bicarbonate.

The lubrication fluid may be an oil or grease comprising an aliphatic, hydrocarbon, organic, or silicone material. The said lubrication fluid may be emulsified or dispersed in an aqueous carrier. A silicone oil or grease may be dispersed in an aqueous carrier or in an aliphatic, organic, or hydrocarbon oil or grease.

The aluminate compound may be emulsified or dispersed in the lubrication fluid by any convenient means, such as by use of an agitator, a recycle pump, a sonic mixer, or an in-line static mixture; a dispersing aid or additive is usually beneficial.

The amount of the aluminate compound which is used in the lubrication fluid is usually from about 0.1% by weight to as much as 10% or more by weight. Preferably, the amount of aluminate compound in the lubrication fluid is about 0.2% to about 2.0% by weight.

The embodiments of tests and examples which follow are to illustrate the invention, but the invention is not limited to the particular embodiments illustrated.

Load-Capacity Tests

Figure 1:
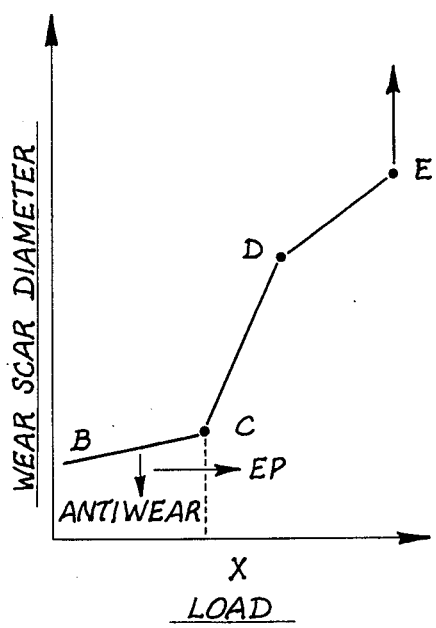
FIG. 1 is an illustration, not to scale, for use as a visual aid in describing wear rates in load-capacity tests.

Load-capacity tests are generally used to determine the ability of a lubricant to prevent severe adhesive wear or seizure; they consist of wear tests run at different and progressively high loads in a 4-ball wear test apparatus. The diameter of wear scars produced on the balls at a given load are measured. With reference to FIG. 1, it is illustrated that the wear scar diameter may gradually increase (line BC) as the load (X) is increased until a transition region (line CD on FIG. 1) is reached where the wear rate is substantially increased and the slope of the line is steep. Further increases in pressure result in an incipient seizure region (line DE of FIG. 1) until contact junction temperatures are elevated so high that the lubricating film is rendered ineffective (at point E) and massive adhesion then leads to welding.

The 4-ball wear test apparatus is a widely used means for evaluating lubricants and lubricant additives under heavy loads, i.e., extreme pressure. For the tests disclosed here, a test device, sold under the tradename "Falex Model No. 6 Friction and Wear-Test Machine", with 4-ball test adapter, was employed using four 0.5-inch bearing balls (AISI-E-52100, grade 25) with roundness specification of $6.35 \times 10^{-4}$ mm. In the test there are three balls (each touching the other two) in a cup which rests in a stationary specimen holder. The fourth ball is placed on top of (and in respective contact with) the three balls; this fourth ball is held in place by an upper specimen holder which affixes to a vertically-disposed spindle. The lower specimen holder is supported by a lower shaft which is equipped with means for measuring wear rate and torque. Thermocouples inserted into wells in the wall of the four-ball cup are used, as needed, in measuring the temperature during the test.

Friction and Wear Tests

Bench wear tests are often used to evaluate anti-wear and extreme pressure characteristics of lubricants. In this study, the Falex four-ball wear test method for evaluating the EP/anti-wear characteristics of paraffinic (e.g., Rubrex-100 oil), paraffinic-naphthalhenic blend (e.g. Flowrex-200 oil) oils with and without additives were examined. The Falex friction and wear tester was chosen because of its availability and because it facilitates the acquiring of torque versus wear cycle data on real time basis for determination of coefficient of friction or wear coefficient. The four-ball test is used extensively in industry for wear testing. The test is easy to conduct, well controlled and uniform test specimens are available at low cost. In wear testing, the specimens basically undergo a destructive evaluation process. In the four-ball test, bearing balls (AlSl-E-52100, grade 25) with roundness specification of $6.35 \times 10^{-4}$ mm are readily available. In experiments employing the four-ball machine, wear is generally determined by measuring the average scar diameter.

Four-Ball Test Conditions

The extreme pressure and the anti-wear lubrication properties of the experimental additive lithium stearate aluminate were evaluted by four-ball tests. Test loads were varied from 22.6 to 90.4 Kgf (50–200 lbs). These correspond to an approximate Hertzian contact pressure of 1750–7000 $N/m^2$ (25,000–100,000 psi). The test speed was 1000 RPM and each test ran for 50 minutes. Approximately 15–20 cc of fluid was used for each test. Before each test is conducted, the balls, top ball chuck and sample container are thoroughly washed with reagent grade hexane, toluene and acetone. The specimen holder and balls were dried at 75° C., then cooled to room temperature prior to the test run. The upper spindle was rinsed with toluene. After the tests were over, optical microscope pictures were taken and the scar diameters were measured from these pictures. During each test run, the torques, as a function of the wear cycles, were monitored on a real time data acquisition basis for data analyses.

In accordance with the procedures which are described in the operating manual which accompanies the Falex testing device, said procedures apparently having been adapted from existing ASTM procedures, the following experiments are carried out:

EXAMPLE 1

The effect of various concentrations of LSA in a commercially available lubricant sold under the tradename "Rubrex" oil is tested in the 4-ball tester at 100 lb. load for 50 minutes and the following data (Table I) indicate the effect on wear rate.

TABLE I

| Concentration of LSA in Rubrex oil (wt. %) | Average wear scar diameter (mm) |
| --- | --- |
| 0 | 0.96 |
| 0.24 | 0.73 |
| 0.5 | 0.67 |
| 1.0 | 0.63 |
| 1.5 | 0.62 |

EXAMPLE 2

The effect on wear scar diameter vs. LSA concentration of different particle sizes (viz. 150 Å and 4000 Å) on a commercially available lubricant sold under the tradename "Flowrex" oil is tested as in Example 1 except that the load is 150 lb. and the duration is 50 minutes. Table II illustrates the results.

TABLE II

| Concentration of LSA in Flowrex oil, %/Å | Average wear scar diameter (mm) |
| --- | --- |
| 0/0 | 0.83 |
| 0.25/150 | 0.80 |
| 0.25/4000 | 0.67 |
| 0.5/150 | 0.65 |
| 0.5/4000 | 0.64 |
| 1.0/150 | 0.66 |
| 1.0/4000 | 0.57 |
| 1.5/150 | 0.66 |
| 1.5/4000 | 0.56 |

EXAMPLE 3

Various amounts of LSA in Rubrex oil are found to reduce the coefficient of friction of the oil. Data are in Table III.

TABLE III

| Concentration of LSA in Rubrex oil (wt. %) | Torque, inch/lbs | Friction Reduction (%) |
| --- | --- | --- |
| 0 | 2.2 | — |
| 0.25 | 2.0 | 9 |
| 0.50 | 1.6 | 27 |
| 1.0 | 1.7 | 23 |
| 1.5 | 1.7 | 23 |

EXAMPLE 4

Various amounts of LSA in Flowrex oil are found to reduce the coefficient of friction of the oil. Data are in Table IV.

TABLE IV

| Concentration of LSA in Flowrex oil (wt. %) | Torque, inch/lbs | Friction Reduction (%) |
| --- | --- | --- |
| 0 | 2.9 | — |
| 0.25 | 2.6 | 10 |
| 0.50 | 2.8 | 3 |
| 1.0 | 2.25 | 22 |
| 1.5 | 2.2 | 24 |

EXAMPLE 5

The average scar diameter of Flowrex-200 oil (a naphthenic-paraffinic oil) is measured, and compared with portions of the same oil containing, respectively, 1% by wt. of lithium stearate and 1% by wt. of LSA. With reference to FIG. 1 attached hereto, it is found that the values of X at points B, C and D are as follows, with average scar diameter, in mm, shown in parentheses.

TABLE V

| Sample | Load at Point B (kg) | Load at Point C (kg) | Load at Point D (kg) |
|---|---|---|---|
| Flowrex-200 oil* | 22 (.61 mm) | 59 (.60 mm) | 68 (.80 mm) |
| Flowrex-200 oil* containing 1% by wt. stearic acid | 22 (.62 mm) | 45 (.57 mm) | 68 (.82 mm) |
| Flowrex-200 oil containing 1% by wt. LSA | 22 (.52 mm) | 77 (.58 mm) | 90 (.80 mm) |

*for comparison with present invention.

There is found little change in the average scar diameter of each of the above three samples between points B and C, but additional increased loads, greater than at point C, gives a steep climb in the curve of the average scar diameter, indicating that the transition range has been reached.

EXAMPLE 6

Figure 2:
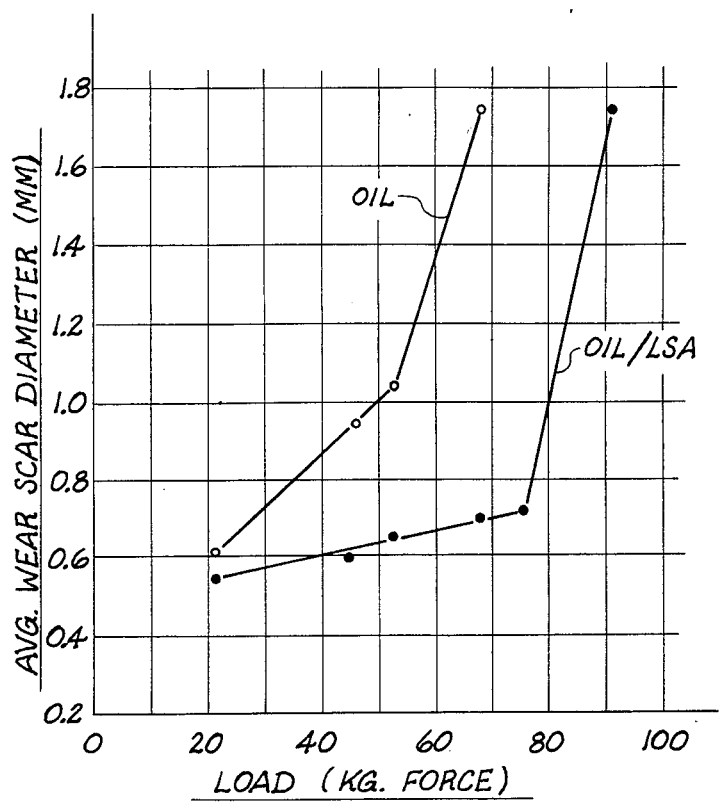
FIG. 2 illustrates curves for wear scar diameter vs. increasing load for an oil and for the oil with LSA added thereto.

FIG. 2 attached hereto illustrates the wear scar curves vs. increasing loads for a paraffinic oil (i.e. Rubrex-100 oil) and for the same oil with 1% by wt. of LSA added thereto. The LSA not only extends the load carrying capacity (from about 52 Kgf to about 75 Kgf) but also reduces the scar diameter at a given load.

EXAMPLE 7

Figure 3:
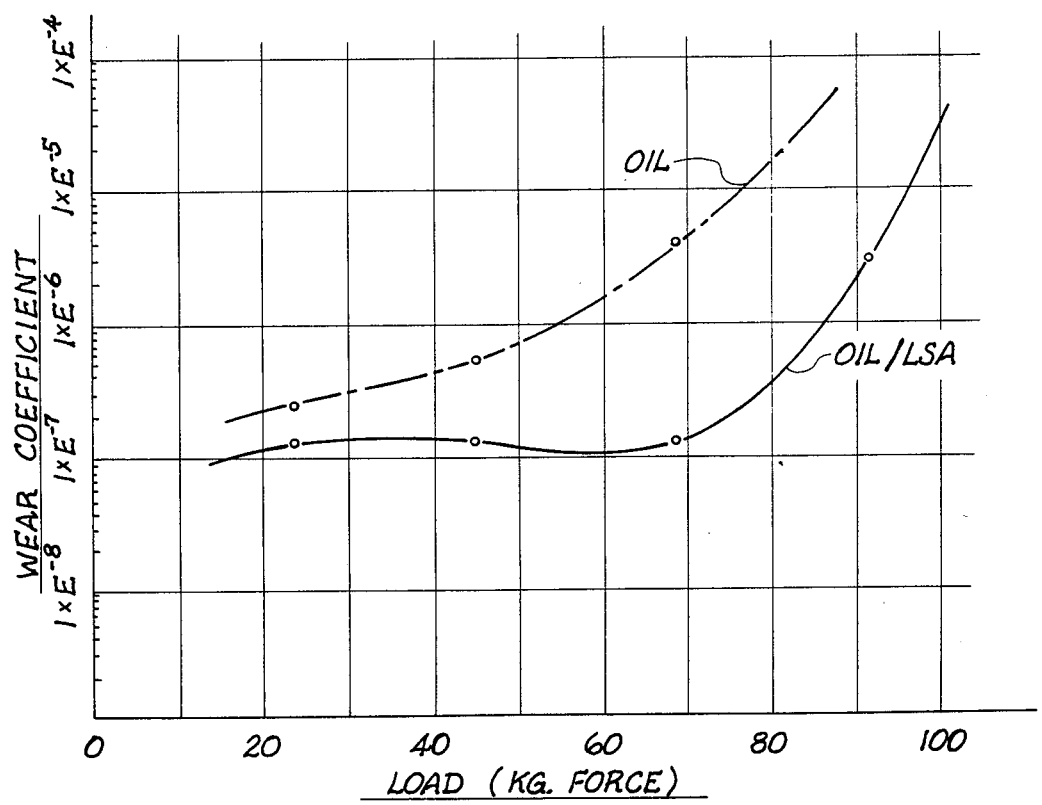
FIG. 3 illustrates the improvement in wear coefficient obtained by adding LSA to an oil.

FIG. 3 attached hereto illustrates the wear coefficient v. increasing loads for Rubrex oil and for Rubrex oil with 1% by wt. of LSA additive.

EXAMPLE 8

Tests were made using various compounds which conform essentially to formula I or II as described in the Summary of the Invention, supra.

The following Table VI shows data obtained using 1% by wt. of the additive in a lubrication oil, Flowrex-200 (Mobil Oil), which exhibits a viscosity of 40 cst at 40° C. The tests were made using a Four-Ball method according to ASTM D-2266 under a constant force of 20 kg at 1800 rpm for 1 hour at 130° F. (54.4° C.).

TABLE VI

| Flowrex-200 Plus 1% Additive | No. of c's in Fatty Acid | Wear Scar Diameter (mm)* |
|---|---|---|
| Control, no additive | — | 0.61 |
| Lithium Stearate Aluminate (LSA) | 18 | 0.55 |
| Lithium Laurate Aluminate | 12 | 0.65 |
| Calcium Stearate Aluminate | 18 | 0.59 |
| Lithium Decanoate Aluminate | 10 | 0.66 |
| Zinc Stearate Aluminate | 18 | 0.54 |
| Lithium Behenate Aluminate | 22 | 0.73 |

*In this test a scar diameter of 0.8 mm or less is considered passing.

EXAMPLE 9

The break point (i.e. point C at load X as illustrated in FIG. 1) of various embodiments are shown in Table VII, all samples using 1% additive in the Flowrex-200 as in Example 8, but using increases in the force applied.

TABLE VII

| Oil Plus 1% Additive | No. of c's in Fatty Acid | Average Wear Scar Diameter (mm) | Break Point lbs/kg |
|---|---|---|---|
| Control, no additive | — | 0.63 | 124/56.3 |
| Lithium Adipate Aluminate | 6 | 0.65 | 131/59.5 |
| Lithium Decanoate Aluminate | 10 | 0.66 | 160/72.6 |
| Lithium Laurate Aluminate | 12 | 0.65 | 166/75.4 |
| Calcium Stearate Aluminate | 18 | 0.59 | 165/74.9 |
| Zinc Stearate Aluminate | 18 | 0.54 | 150/68.1 |
| Lithium Stearate Aluminate (LSA) | 18 | 0.55 | 180/81.7 |
| Lithium 12-OH—Stearate Aluminate | 18 | 0.68 | 150/68.1 |
| Lithium Behenate Aluminate | 22 | 0.73 | 175/79.5 |

*Average wear scar up to the break point.

In the above Tables VI and VII the listed compounds conform, essentially, to generic formula I or II as illustrated below by the approximate chemical formula shown.

| Trivialized Name* | Chemical Formula |
|---|---|
| Lithium Adipate Aluminate | $Li(C_6H_8O_4)_{0.5}.2Al(OH)_3$ |
| Lithium Decanoate Aluminate | $Li(C_{10}H_{19}O_2).2Al(OH)_3$ |
| Lithium Laurate Aluminate | $Li(C_{12}H_{23}O_2).2Al(OH)_3$ |
| Calcium Stearate Aluminate | $Ca_4(C_{18}H_{34}O_2)_4(SO_4)_2.2Al(OH)_3$ |
| Zinc Stearate Aluminate | $Zn_4(C_{18}H_{34}O_2)_4(SO_4)_2.2Al(OH)_3$ |
| Lithium Stearate Aluminate | $Li(C_{18}H_{35}O_2).2Al(OH)_3$ |
| Lithium 12-HO—Stearate Aluminate | $Li(HO-C_{18}H_{34}O_2).2Al(OH)_3$ |
| Lithium Behenate Aluminate | $Li(C_{22}H_{43}O_2).2Al(OH)_3$ |

*Li compounds are formula I, Ca and Zn compounds are formula II.

I claim:

1. A method for improving the anti-friction properties of lubrication fluids subjected to intensive shearing or grinding forces, said method comprising
uniformly dispersing in said fluid, as small particles, at least one crystalline aluminate conforming substantially to the formulae

$$Li(R)_r^v.2Al(OH)_3.nH_2O, \qquad \text{I.}$$

and

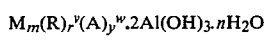
$$M_m(R)_r^v(A)_y^w.2Al(OH)_3.nH_2O \qquad \text{II.}$$

where
$nH_2O$ represents any waters of hydration that may be present;
R represents a monocarboxylic acid or dicarboxylic acid of $C_6-C_{22}$, including those which are OH-substituted;
r is greater than zero and represents the number of R ions in the molecule;
v is the valence of R, being monovalent or divalent,
M is divalent Zn or Ca cations;
A represents inorganic anions of valence 1–3, represented by w;
y is equal to or greater than zero and represents the number of A anions;
wherein, in formula I, vr represents an amount of R anions to substantially satisfy the valence requirements of Li;
wherein, in formula II, r>y and (vr+wy) represents an amount of combined anions, R and A, to substantially satisfy the valence requirements of M;

with m representing the number of divalent M cations and having a numerical value in the range of about 1 to about 4.

2. The method of claim 1 wherein the lubrication fluid is selected from the group consisting of oils or greases of a hydrocarbon, aliphatic, organic, or silicone material.

3. The method of claim 1 wherein the amount of the aluminate dispersed in said lubrication fluid comprises about 0.1% to about 10% by weight of the total.

4. The method of claim 1 wherein the particles of the aluminate dispersed in said lubrication fluid are of a size in the range of about 150 to about 5000 angstroms.

5. The method of claim 1 wherein the dispersing is performed by the use of an agitator, a recycle pump, a sonic mixer, or an in-line static mixer.

6. The method of claim 1 wherein the lubrication fluid comprises an oil or grease emulsified or dispersed in an aqueous carrier.

7. The method of claim 1 wherein the lubrication fluid comprises an organic lubrication material emulsified or dispersed in an aqueous carrier.

8. The method of claim 1 wherein the lubrication fluid comprises an aliphatic oil or grease emulsified or dispersed in an aqueous carrier.

9. The method of claim 1 wherein the lubrication fluid comprises a hydrocarbon oil or grease emulsified or dispersed in an aqueous carrier.

10. The method of claim 1 wherein the lubrication fluid comprises a silicone oil or grease.

11. The method of claim 1 wherein the lubrication fluid comprises a silicone oil or grease emulsified or dispersed in an aqueous carrier.

12. The method of claim 1 wherein the lubrication fluid comprises a silicone oil or grease dispersed in an aliphatic oil or grease carrier.

13. The method of claim 1 wherein the amount of the aluminate dispersed in said lubrication fluid comprises about 0.2% to about 2.0% by weight of the total.

14. The method of claim wherein the aluminate is at least one of formula I, excluding $LiR.2Al(OH)_3.nH_2O$ where R is the anion of stearic acid.

15. The method of claim 1 wherein the aluminate is at least one of formula I wherein R is the anion of adipic acid, decanoic acid, lauric acid, hydroxy-stearic acid, and behenic acid.

16. The method of claim 1 wherein the aluminate is at least one of formula II.

17. The method of claim 1 wherein the aluminate is at least one of $Ca_4(C_{18}H_{34}O_2)_4(SO_4)_2.2Al(OH)_3$ or $Zn_4(C_{18}H_{34}O_2)_4(SO_4)_2.2Al(OH)_3$.

* * * * *

UNITED STATES PATENT AND TRADEMARK OFFICE
CERTIFICATE OF CORRECTION

PATENT NO.   : 4,610,797
DATED        : September 9, 1986
INVENTOR(S)  : Kishore K. Kar and John L. Burba, III It is certified that error appears in the above—identified patent and that said Letters Patent is hereby corrected as shown below:

In Item [75] on the cover sheet, the name --John L. Burba, III-- should have been included.

Col. 10, line 15; insert --1-- after "Claim".

Signed and Sealed this

Seventh Day of April, 1987

Attest:

DONALD J. QUIGG

Attesting Officer

Commissioner of Patents and Trademarks